Figure 1:
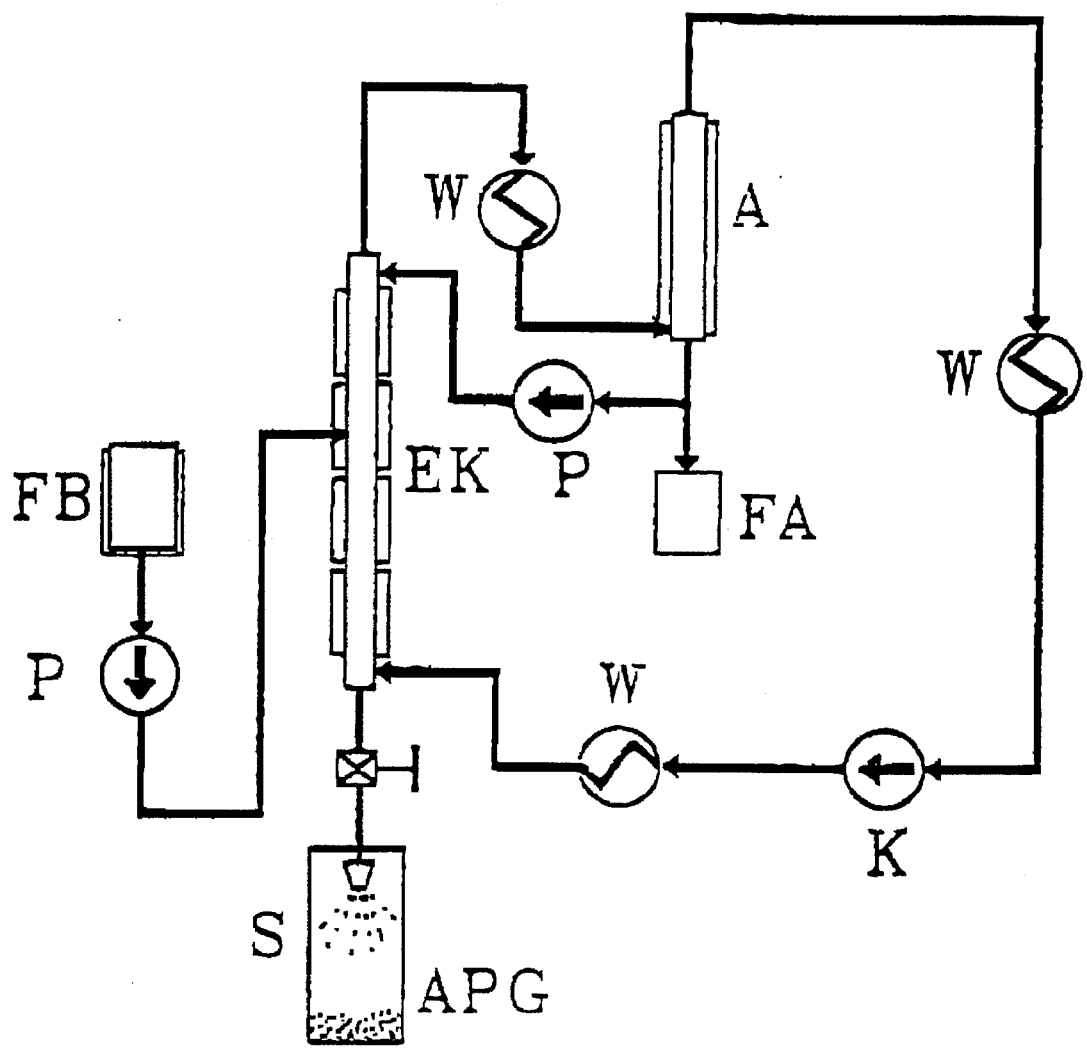

United States Patent [19]
Grüning et al.

[11] Patent Number: 5,646,258
[45] Date of Patent: Jul. 8, 1997

[54] METHOD OF SYNTHESIZING ALKYL GLUCOSIDES

[75] Inventors: Burghard Grüning, Essen; Siegfried Peter, Uttenreuth-Weiher; Manfred Recksik, Essen; Eckhard Weidner; Zhengfeng Zhang, both of Erlangen, all of Germany

[73] Assignee: M. Goldschmidt AG, Essen, Germany

[21] Appl. No.: 555,564

[22] Filed: Nov. 8, 1995

[30]     Foreign Application Priority Data

Nov. 18, 1994 [DE] Germany ............... 44 41 072.7

[51] Int. Cl.⁶ ......................................... C07H 1/00
[52] U.S. Cl. ............................... 536/18.6; 536/124
[58] Field of Search ........................ 536/18.6, 124

[56]               References Cited

U.S. PATENT DOCUMENTS 3,839,318  10/1974  Mansfield ................. 536/18.6

FOREIGN PATENT DOCUMENTS

| | | |
|---|---|---|
| 0404226 | 12/1990 | European Pat. Off. . |
| 0526710 | 2/1993 | European Pat. Off. . |
| 3833780 | 4/1990 | Germany . |
| 3932173 | 4/1991 | Germany . |
| 3940827 | 6/1991 | Germany . |
| 4019175 | 1/1992 | Germany . |

*Primary Examiner*—Elli Peselev
*Attorney, Agent, or Firm*—Anderson Kill & Olick PC

[57]               ABSTRACT

A method for synthesizing alkyl glucosides by the acetalization of sugars, particularly glucose, with alcohols in excess and subsequent separation of the excess alcohol by extraction, the extraction being carried out with an extraction agent, which is close to the critical point at a reduced pressure in the range of 0.8 to 1.3 and preferably of 0.9 to 1.2 at pressures, which are selected so that the density of the extraction agent, which is close to the critical point, is greater than 180 kg/m³.

13 Claims, 1 Drawing Sheet

METHOD OF SYNTHESIZING ALKYL GLUCOSIDES

FIELD OF INVENTION

The invention relates to a method for synthesizing alkyl glucosides, which are frequently also referred to as alkyl polyglucosides in the literature, by the acetalization of sugars, particularly glucose, with alcohols in excess and subsequent separation of the excess alcohol by extraction.

BACKGROUND INFORMATION AND PRIOR ART

From the German Offenlegungsschrift 38 33 780, a method is known for the direct synthesis of alkyl glucosides by the acetalization reaction of higher primary alcohols with sugars, particularly with glucose, in which (in abbreviated quotation)

a) mixtures of an aliphatic, primary alcohol, glucose and an acidic catalyst are reacted at an elevated temperature,
b) the molar ratio of glucose to aliphatic alcohol is 1:2 to 1:10,
c) the reaction mixture is kept at an elevated temperature and a reduced pressure until the water of reaction is removed completely,
d) the reaction mixture is cooled to 90° C. and a base is added to neutralize the catalyst and adjust the pH to at least 8, whereupon the normal pressure is restored,
e) the excess alcohol is distilled off gently to a value of less than 5% by weight, and
f) water is added to form a paste and the product is bleached with active oxygen at a pH of 8 to 10.

The German Offenlegungsschrift 39 32 173 relates to a method for the distillative separation of alcohols with chain lengths up to 30 and particularly with chain lengths between 8 and 18 carbon atoms, from a mixture of alkyl glucosides and alcohols not reacted during the synthesis of these alkyl glucosides, the alcohols being removed in two steps, with the distinguishing feature that a falling film evaporator is used in the first step and a thin-layer evaporator in the second step.

Distillative removal of the alcohol imposes an appreciable thermal burden, which is associated with the danger that the product will darken. This goes so far, for example, in the case of stearyl glucoside, that the removal of stearyl alcohol under industrial conditions is practically impossible, without affecting the quality of the stearyl glucoside appreciably. For this reason, various methods for bleaching alkyl glucosides have been described, for example, in EP-OS 0 526 710, the DE-OS 40 19 175 and the DE-OS 39 40 827, in which bleaching is carried out by irradiation, the addition of hydrogen peroxide or the treatment with ozone. At the present time, no method is known, which avoids the critical effect of heat on the crude product, consisting of alkyl glucoside and alcohol, and thus does not lead to the dark coloration.

The purification of sugar surfactants by treatment with carbon dioxide above the critical point has been described in the European patent application 0 404 226. The products, subjected to the extraction, contain esters of a non-reducing sugar and one or several fatty acids. For this method, the extraction must be carried out discontinuously since, at the conclusion of the removal of the fatty acids, the product is present in solid form and the separation process must therefore be interrupted to discharge the end product.

OBJECT OF THE INVENTION

An object of the present invention is a method for the synthesis of alkyl glucosides by the acetalization of sugars, particularly of glucose, with alcohols in excess and subsequent separation of the excess alcohol by extraction. The method is characterized in that the extraction is carried out with an extraction agent, which is close to the critical point, at a reduced pressure ranging from 0.8 to 1.3 and preferably from 0.9 to 1.2, selected so that the density of the extraction agent, which is close to the critical point, is not less than 180 kg/m$^3$.

SUMMARY OF THE INVENTION

Preferably, a hydrocarbon with 2 to 8 carbon atoms is used as an extraction agent close to the critical point.

A different version of a method for extracting excess alcohol is characterized in that the extraction is carried out with an ether, which has 2 to 6 carbon atoms and a density of not less than 180 kg/m$^3$, at temperatures greater than 90° C. and a pressure greater than 30 bar.

It is a particular advantage of the inventive method that, under the extraction conditions, the phase, which contains the alcohol-free alkyl glucosides in equilibrium with the extraction agent, is liquid so that alkyl glucosides of high purity can be obtained continuously.

Over all, the method of this invention offers the following advantages:

a) the alcohols can be removed completely;
b) the extraction can be carried out continuously; and countercurrently
c) the extraction agents can be removed completely at low temperatures.

The reduced temperature (Tr) is understood to be the number obtained by dividing the measured temperature in Kelvin by the critical temperature (Tc) of the system in Kelvin according to the following formula $$Tr=T/Tc$$

Extracting with hydrocarbons, particularly with propane, is preferred.

Up to 10% of lower molecular weight aliphatic solvents and/or water can be added to the extraction agent. Examples of aliphatic solvents are aliphatic alcohols, such as methanol, ethanol and isopropanol, ketones, such as acetone and methyl ethyl ketone and acids, such as formic acids and acetic acid. Ethanol is preferred.

Of the aforementioned extraction agents, propane, butane and dimethyl ether are particularly preferred because of their low boiling point (the boiling point of propane is −44.5° C., of butane −0.5° C. and of dimethyl ether −24.9° C.). They are suitable as extraction agents for the inventive method if their density is more than 180 kg/m$^3$ and, preferably, 200 to 600 kg/m$^3$. Particularly effective is a procedure with an extraction agent at a reduced temperature ranging from 0.8 to 1.3 at correspondingly elevated pressures.

As alkyl glucosides, which are to be freed from unreacted alcohol by the inventive method, particularly compounds of the general formula

come into consideration. In the above formula, the groups have the following meanings:
$R^1$=a hydrocarbon group with 3 to 21 carbon atoms,
$R^2$=CH$_2$, (C$_n$H$_{2n}$O)$_m$ wherein n has an average numerical value of 2 to 4 and preferably of 2 to 3, and
m has an average numerical value of 1 to 30 and preferably of 1 to 10, G=a group derived from an aldose or ketose with 5 or 6 carbon atoms and preferably a group derived from glucose, a=an average numerical value of 1 to 10 and preferably of 1 to 6.

It follows from this that the excess alcohols, which are to be removed, correspond to the formula $R^1-R^2-OH$, in which $R^1$ and $R^2$ have the meaning already given. Preferably, the alcohol, which is to be removed, is a fatty alcohol with 8 to 22 carbon atoms.

The alcohols can be removed continuously or discontinuously by a countercurrent method.

The invention is described in greater detail by FIG. 1, which shows an extraction apparatus suitable for carrying out the method.

Because of the economic advantages, the inventive method preferably is carried out continuously and countercurrently. The apparatus, shown diagrammatically in FIG. 1, consists essentially of an extraction column (separation column) and a precipitation column (regenerating column).

After being preheated to about 130° C., the mixture of, for example, fatty alcohol and alkyl glucosides is pumped into the separating column at the desired height, preferably in the center of the column. The extraction agent advisably is added to the bottom of the column and flows through it from the bottom to the top. The pressure and temperature are adjusted so that the mixture of the product of low volatility and the extraction agent splits into two liquid phases. The fatty alcohols and a slight amount of alkyl glucosides dissolve in the extraction agent. A mixture of fatty alcohols, extraction agent and a small amount of alkyl glucosides leaves the extraction column at the head and is transferred to the regenerating column. By increasing the temperature and/or decreasing the pressure, conditions are adjusted in the regenerating column, under which the extraction agent is present as a vapor of so low a density, that the extracted materials precipitate out quantitatively.

The extraction agent leaves the regenerating column at the head in the vapor state. It is condensed in a heat exchanger and returned to the extraction column. A portion of the product, which has precipitated in the regenerating column, advisably is recycled and pumped back to the head of the extraction column. The remaining portion of the extracted fatty alcohols is drawn off at the sump of the regenerating column and the pressure is relieved to atmospheric pressure. The gaseous extraction agent, released in the process, can be recompressed, condensed or incinerated. The extracted fatty alcohols can be returned to the reactor for alkyl glucoside synthesis.

As a result of their higher density, the alkyl glucosides in the extraction column flow downwards and, in so doing, are freed from fatty alcohols. The pure alkyl glucosides, so obtained, are drawn off in the sump of the extraction column. The extraction agent is removed completely by relieving the pressure to atmospheric pressure in a spraying apparatus and the refined material is obtained in the form of a finely divided, solid powder. At the same time, the temperature before the spraying is adjusted so that the enthalpy content of the liquid to be sprayed is sufficient to cover the evaporation enthalpy of the solvent and the final temperature of the sprayed material lies below the softening temperature of the powder formed.

In order to ensure that there are two phases during the extraction process, the extraction column advisable is equipped with facilities for producing a temperature profile. As already mentioned, the temperature at the head of the extraction column is adjusted to be 10° to 80° C. and preferably 20° to 50° C. higher than the temperature in the column sump. Inline heat exchangers, for example, may be used to produce this temperature gradient. In this way, it is ensured that two phases exist in the column at all mixing ratios of fatty alcohols to alkyl glucosides.

The invention is described in greater detail in the following examples. Examples 1 to 6 describe the separation of crude mixtures of alcohol and alkyl glucoside under the inventive conditions. From the compositions of the respective gaseous and liquid phases, it becomes clear that an accumulation of the alcohols takes place in the gaseous phase and an accumulation of alkyl glucosides takes place in the liquid phase. The magnitude of the resulting separation factors is sufficient in every case for increasing the concentration of more than 95% of the alkyl glucosides or the alcohols in a continuous, multi-step process. The abbreviation n.d. stands for not detectable. The percentages given are percentages by weight. It is understood that these Examples are by way of illustration and not by way of limitation.

EXAMPLE 1

An alkyl glucoside is synthesized by a method based on that of U.S. Pat. No. 3,839,318 from fatty alcohol, which consists essentially of dodecyl alcohol and tetradecyl alcohol, and anhydrous glucose. The composition of the crude product, according to analysis (silylation and high-temperature gas chromatography) is as follows:

| decanol | 0.9% | monoglucoside | 14.7% |
|---|---|---|---|
| dodecanol | 58.7% | diglucoside | 3.4% |
| tetradecanol | 19.3% | triglucoside | 1.3% |
| hexadecanol | 1.0% | tetraglucoside | 0.4% |
| | | pentaglucoside | 0.2% |
| total fatty alcohol | 79.9% | total alkyl glucosides | 20.0% |

In an electrically heated, 1 L shaking autoclave, 250 g of the crude product are heated slowly. When the temperature reaches 116° C., propane is pumped in until the pressure has been built up to 58 bar. For this purpose, approximately 170 g of propane are required. Shaking the autoclave ensures thorough mixing. When the autoclave is at rest, the mixture rapidly separates into a liquid and a gaseous phase. Samples are taken with the help of a capillary with an internal diameter of 0.3 mm. After 30 minutes, the composition of the phases no longer changes. Their composition is determined by evaporation of the propane and high-temperature gas chromatography.

Composition of the gaseous phase, excluding the propane:

| decanol | 1.2% |
|---|---|
| dodecanol | 74.4% |
| tetradecanol | 22.8% |
| hexadecanol | 1.2% |
| total fatty alcohol | 99.6% |

Composition of the liquid phase excluding the propane:

| decanol | 0.7% | monoglucoside | 27.2% |
|---|---|---|---|
| dodecanol | 47.2% | diglucoside | 6.1% |
| tetradecanol | 16.0% | triglucoside | 2.2% |
| hexadecanol | 0.8% | tetraglucoside | 0.6% |
| | | pentaglucoside | 0.2% |
| total fatty alcohol | 64.7% | total alkyl glucosides | 36.3% |

In the gaseous phase, there are 10.7% of the non-volatiles and, in the liquid phase, 61%. The gaseous phase contains 89.3% propane, the liquid phase 39.0%.

EXAMPLE 2

The example is carried out with the same raw material, employing a method similar to that of Example 1. Contrary to Example 1, propane is pumped into the autoclave, until the pressure is 68 bar, for which about 210 g of propane are required. The phases are separated and analyzed.
Composition of the gaseous phase excluding the propane:

| decanol | 1.0% | monoglucoside | 2.1% |
|---|---|---|---|
| dodecanol | 71.5% | diglucoside | 0.4% |
| tetradecanol | 23.6% | triglucoside | 0.1% |
| hexadecanol | 0.7% | | |
| total fatty alcohol | 96.8% | total alkyl glucosides | 2.6% |

Composition of the liquid phase excluding the propane:

| decanol | 0.4% | monoglucoside | 42.4% |
|---|---|---|---|
| dodecanol | 31.4% | diglucoside | 9.5% |
| tetradecanol | 10.6% | triglucoside | 3.4% |
| hexadecanol | 0.5% | tetraglucoside | 1.0% |
| | | pentaglucoside | 0.5% |
| total fatty alcohol | 42.9% | total alkyl glucosides | 56.8% |

In the gaseous phase, there are 26.5% of the non-volatiles and in the liquid phase there are 56.5%. The gaseous phase contains 73.5% propane and the liquid phase 43.5%.

EXAMPLE 3

In an electrically heated, shaking autoclave with a 1 L capacity, 250 g of a starting material, the composition of which corresponds to the crude product of Example 1, are heated slowly. After a temperature of 190° C. is reached, dimethyl ether is pumped in, until the pressure has built up to 80 bar. For this purpose, about 250 g of dimethyl ether are required. Good mixing is ensured by shaking the autoclave. When the autoclave is at rest, the mixture rapidly separates into a liquid and a gaseous phase. Samples are taken with the help of a capillary with an internal diameter of 0.3 mm. After about 20 minutes, the composition of the phases no longer changes. The composition is determined after evaporation of the dimethyl ether by high-temperature gas chromatography.
Composition of the gaseous phase excluding the dimethyl ether:

| decanol | 1.6% | monoglucoside | 0.1% |
|---|---|---|---|
| dodecanol | 80.2% | higher | |
| tetradecanol | 17.7% | glucosides not detectable | |
| hexadecanol | 0.4% | | |
| total fatty alcohol | 99.9% | total alkyl glucosides | 0.1% |

Composition of the liquid phase excluding the dimethyl ether:

| decanol | 0.7% | monoglucoside | 20.4% |
|---|---|---|---|
| dodecanol | 54.7% | diglucoside | 4.4% |
| tetradecanol | 17.7% | triglucoside | 1.4% |
| hexadecanol | 0.6% | tetraglucoside | 0.6% |
| | | pentaglucoside | n.d. |
| total fatty alcohol | 73.2% | total alkyl glucosides | 26.8% |

The gaseous phase contains 92.5% dimethyl ether and 7.5% of fatty alcohols and alkyl glucosides. The liquid phase contains 38% of dimethyl ether.

EXAMPLE 4

From fatty alcohol, which consists essentially of hexadecyl and octadecyl alcohol, and anhydrous glucose, an alkyl glucoside, which is referred to in the following by the abbreviation, stearyl glucoside, is synthesized by a method similar to that of U.S. Pat. No. 3,839,318. The crude product has the following composition:

| tetradecanol | <0.1% | monoglucoside | 26.9% |
|---|---|---|---|
| hexadecanol | 15.6% | diglucoside | 4.6% |
| octadecanol | 50.8% | triglucoside | 2.0% |
| eicosanol | <0.1% | tetraglucoside | <0.1% |
| | | pentaglucoside | <0.1% |
| total fatty alcohol | 66.4% | total alkyl glucosides | 33.6% |

In an electrically heated, shaking autoclave with a capacity of 1 L, 250 g of the stearyl glucoside are heated slowly. After a temperature of 122° C. is reached, propane is pumped in up to a pressure of 70 bar. For this purpose, 250 g of propane are required. Shaking the autoclave ensures good mixing. When the autoclave is at rest, the mixture rapidly separates into a liquid and a gaseous phase. Samples are taken with the help of a capillary with an internal diameter of 0.3 mm. After about 20 minutes, the composition of the phases no longer changes. After evaporation of the propane, the composition of the non-volatile portion, which has remained behind, is determined by high-temperature gas chromatography.
Composition of the gaseous phase excluding the propane:

| dodecanol | <0.1% | monoglucoside | 10.9% |
|---|---|---|---|
| tetracedanol | 0.1% | diglucoside | <0.1% |
| hexadecanol | 20.8% | triglucoside | n.d. |
| octadecanol | 68.2% | tetraglucoside | n.d. |
| eicosanol | n.d. | pentaglucoside | n.d. |
| total fatty alcohol | 89.1% | total alkyl glucosides | 10.9% |

Composition of the liquid phase excluding the propane:

| dodecanol | n.d. | monoglucoside | 62.0% |
|---|---|---|---|
| tetracedanol | 0.2% | diglucoside | 19.0% |
| hexadecanol | 4.5% | triglucoside | <0.1% |
| octadecanol | 14.1% | tetraglucoside | n.d. |
| eicosanol | n.d. | pentaglucoside | n.d. |
| total fatty alcohol | 18.9% | total alkyl glucosides | 81.0% |

The gaseous phase contains 81% propane and the liquid phase 23% propane.

EXAMPLE 5

A 3-neck flask with reflux condenser and water separator is filled with 729 g (5.9 moles) of n-butanol and 5.1 g of p-toluenesulfonic acid monohydrate and heated to 120° C. At this temperature, 300 g (1.66 moles) of anhydrous glucose are added in portions of about 5 g in the course of 1 hour. During this phase, water already separates out as an indication of the progress of the glucoside formation. This reaction is continued at 120° C., until water no longer is formed, as is the case after a few hours. The reaction mixture is cooled to 65° C., made alkaline with 36.6 g of a 5% ethanolic KOH solution (the pH of a 30% solution in 1:2 water/ethanol is about 8) and filtered.

The crude product (150 g), which consists of 60.6% by weight of butanol and 39.4% by weight of butyl glucoside, is heated slowly in an electrically heated 1 L shaking autoclave. When a temperature of 91° C. is reached, propane is pumped in up to a pressure of 35 bar. For this purpose, about 150 g of propane are required. Good mixing is ensured by shaking the autoclave. When the autoclave is at rest, the mixture rapidly separates into a liquid and a gaseous phase. Samples are taken with the help of a capillary with an internal diameter of 0.3 mm. After about 20 minutes, no further change is noted in the composition of the phases. When the propane has been evaporated, the composition of the non-volatile portion is determined by high-temperature gas chromatography.

After removal of the propane, the liquid phase consists of 23.2% by weight of butanol and 76.8% by weight of butyl glucosides and the gaseous phase consists of 83.2% by weight of butanol and 16.8% by weight of butyl glucosides. The gaseous phase contains 69.3% by weight of propane and 30.7% by weight of non-volatiles. The liquid phase contains 9.4% by weight of propane.

EXAMPLE 6

In an electrically heated, shaking autoclave, having a capacity of 1 L, 250 g of a $C_{12}/C_{14}$ fatty alcohol glucoside of the following composition:

| dodecanol | 1.9% | monoglucoside | 70.0% |
|---|---|---|---|
| tetracedanol | 3.0% | diglucoside | 15.5% |
| hexadecanol | 0.4% | triglucoside | 5.3% |
|  |  | tetraglucoside | 1.7% |
|  |  | pentaglucoside | 0.7% |
| total fatty alcohol | 5.3% | total alkyl glucosides | 93.2% | and 30 g of ethanol are heated slowly.

As described in Example 1, the $C_{12}/C_{14}$ fatty alcohol glucoside is synthesized and subsequently freed from the bulk of the fatty alcohol by distillation.

After a temperature of 105° C. is reached, butane is pumped in up to a pressure of 23 bar. Good mixing is ensured by shaking the autoclave. When the autoclave is at rest, the mixture rapidly separates into a liquid phase and a gaseous phase. Samples are taken from the two phases with the help of a capillary with an internal diameter of 0.3 mm and analyzed. The gaseous phase contains 5.8% by weight of fatty alcohols and glucosides. Other than butane and ethanol, the product, dissolved in the gaseous phase, consists of 19.2% by weight of fatty alcohols and 80.6% by weight of alkyl glucosides. Other than butane and ethanol, the liquid phase contains 2.7% by weight of fatty alcohol and 96.8% by weight of alkyl glucosides.

EXAMPLE 7

A mixture (250 g) of fatty alcohols and $C_{12}/C_{14}$ fatty alcohol glucosides, the composition of which corresponds to that of the starting material in Example 6, and 60 g of ethanol are heated slowly in an electrically heated shaking autoclave with a capacity of 1 L to 85° C. After that, propane is pumped in up to a pressure of 40 bar. Good mixing is ensured by shaking the autoclave. When the autoclave is at rest, the mixture rapidly separates into a gaseous and a liquid phase. Samples are taken from the two phases with the help of a capillary having an internal diameter of 0.3 mm. After about 20 minutes, the composition no longer changes. When the propane has been evaporated, the samples are analyzed by high-temperature gas chromatography. The gaseous phase contains 7.9% by weight of fatty alcohols and alkyl glucosides. Other than propane and ethanol, the product, dissolved in the gaseous phase consists of 13.7% by weight of fatty alcohols and 86.0% by weight of alkyl glucosides. Other than propane and ethanol, the liquid phase contains 2.9% by weight of fatty alcohols and 96.6% by weight of alkyl glucosides.

EXAMPLE 8

The alcohols are separated from the product mixture of excess alcohols and alkyl glucosides, as described in Example 1 as a crude product, in the equipment of FIG. 1. The product mixture is pumped into approximately the center of the extraction column (separating column). The column is provided with a Sulzer CY package and with heating elements to control the temperature in the various sections. The number of theoretical separating steps of the column is approximately 4. Propane, at a pressure of about 70 bar, functions as an extraction agent. The temperature in the extraction column increases linearly from the sump of the column, where it is 120° C., to the head of the column, where it is 140° C.

By increasing the temperature towards the head of the extraction column, the solubility of the alkyl glucosides in the dense propane is decreased so that losses of alkyl glucosides, which are associated with the discharge of the fatty alcohols, are slight (less than 3%). The propane, laden with fatty alcohols, is supplied to the precipitation column A. By lowering the pressure to about 30 bar in the precipitation column, the density of the propane at 140° C. is decreased to such an extent, that the dissolved fatty alcohols are precipitated quantitatively. The fatty alcohol mixture is obtained as a propane-containing liquid. A portion of the liquid fatty alcohols, present in the sump of the precipitation column, is pumped back to the head of the extraction column to be recycled.

The gaseous propane, which is above the critical point, leaves the precipitator at the head and is cooled off and condensed in a downstream heat exchanger. Subsequently, the liquid propane is recompressed to the extraction pressure of 70 bar and returned to the extraction column by way of a heat exchanger, in which it is heated to the temperature of the sump of the extraction column.

The mixture to be separated flows into the extraction column downwards, countercurrently to the propane and, at the same time always comes into contact with pure propane. The fatty alcohols are largely removed by this countercurrent procedure. The pressure on the sump product from the extraction column is relieved to atmospheric pressure through a spraying nozzle. The pressure is relieved in a spray tower. At the same time, the dissolved propane evaporates completely and, in so doing, cools the alkyl glucosides, which have been freed from fatty alcohols and are obtained as a finely divided powder, to temperatures of less than 60° C.

The analyses of the starting material, refined material and extract are compared below. The sump product, which is rich in glucosides, is referred to as refined material and the head product (which is rich in fatty alcohols) of the precipitation column is referred to as extract.

|  |  | Starting Material % by wt. | Refined Material % by wt. | Extract % by wt. |
|---|---|---|---|---|
| Fatty alcohol: | C 10 | 0.8 | <0.1 | 0.9 |
|  | C 12 | 60.1 | 0.1 | 74.0 |
|  | C 14 | 20.0 | <0.1 | 24.0 |
|  | C 16 | 1.0 | <0.1 | 0.9 |
|  | C 18 | n.d. | <0.1 | <0.1 |
|  | C 20 | n.d. | n.d. | n.d. |
| Total fatty alcohol |  | 81.9 | 0.1 | 99.8 |
| Glucoside: | mono- | 13.4 | 72.7 | 0.19 |
|  | di- | 3.2 | 19.0 | 0.01 |

-continued

|  |  | Starting Material % by wt. | Refined Material % by wt. | Extract % by wt. |
|---|---|---|---|---|
|  | tri- | 1.1 | 6.8 | n.d. |
|  | tetra- | 0.4 | 1.4 | n.d. |
|  | penta- | <0.1 | <0.1 | n.d. |
| Total glucosides |  | 18.1 | 99.9 | 0.2 |

FIG. 1: Schematic flow chart for removing alcohol from mixtures of alcohols and alkyl glucosides with the help of a continuous countercurrent extraction.
A: Precipitation column
EK: Extraction column
FB: Feed container
P: Pump
W: Heat exchanger
APG: Alkyl glucoside
FA: Alcohol
K: Circulating gas compressor
S: Spray tower

What is claimed is:

1. A method for synthesizing alkyl glucosides by acetalizing a sugar with an excess amount of an alcohol and subsequently separating the excess alcohol by extraction, comprising the steps of extracting the alcohol with an extraction agent, close to a critical point, at a reduced pressure in the range of 0.8 to 1.3 provided that the density of the extraction agent, close to the critical point, is greater than 180 kg/m$^3$.

2. The method of claim 1, wherein the extraction agent close to the critical point is a hydrocarbon having 2 to 8 carbon atoms.

3. The method of claim 1, wherein the extraction agent close to the critical point is a saturated hydrocarbon having 3 to 8 carbon atoms.

4. The method of claim 1, wherein the extraction agent close to the critical point is an ether with 2 to 8 carbon atoms.

5. The method of claims 1 or 4, wherein the extraction agent close to the critical point is dimethyl ether.

6. The method of claims 1 or 4, wherein the extraction agent close to the critical point is ethyl methyl ether.

7. The method of claims 1 or 2, wherein the extraction agent close to the critical point is propane, butane or a mixture thereof.

8. The method of claims 1, 2 or 4, wherein the boiling point of the extraction agent used is below the room temperature.

9. The method of claims 1, 2 or 4, wherein the extraction is carried out at a pressure, which is up to about 80 bar higher than the vapor pressure of the extraction agent above the solution.

10. The method of claims 1, 2 or 4, wherein the extraction is carried countercurrently in several steps.

11. The method of claims 1, 2 or 4, wherein the pressure on the refined material, which is drawn off the bottom of an extraction column or a separation column, is relieved through a spray nozzle and that the product, freed from alcohols, is obtained in the form of a powder.

12. The method of claims 1, 2 or 4, wherein a mixture of ether and hydrocarbon is used as an extraction agent.

13. The method of claims 1, 2 or 4, wherein a low molecular weight aliphatic solvent, water or both are added in an amount of up to 10% by weight to the hydrocarbons or ethers used as an extraction agent.

* * * * *

UNITED STATES PATENT AND TRADEMARK OFFICE
CERTIFICATE OF CORRECTION

PATENT NO. : 5,646,258
DATED : 8 July 1997
INVENTOR(S) : Burghard Gruning, et al.

It is certified that error appears in the above-indentified patent and that said Letters Patent is hereby corrected as shown below:

Title page, should read;

{73} Assignee: TH. GOLDSCHMIDT AG. Essen Germany

Signed and Sealed this

Twenty-first Day of October 1997

Attest:

BRUCE LEHMAN

Attesting Officer

Commissioner of Patents and Trademarks